United States Patent [19]

Kisfaludy et al.

[11] 4,386,073
[45] * May 31, 1983

[54] TRIPEPTIDES ACTING ON THE CENTRAL NERVOUS SYSTEM AND A PROCESS FOR THE PREPARATION THEREOF

[75] Inventors: Lajos Kisfaludy; Tamás Szirtes, both of Budapest; Lajos Baláspiri, Szeged; Éva Pálosi, Budapest; László Szporny, Budapest; Ádám Sarkadi, Budapest, all of Hungary

[73] Assignee: Patentbureau DANUBIA, Budapest, Hungary

[*] Notice: The portion of the term of this patent subsequent to Nov. 10, 1998, has been disclaimed.

[21] Appl. No.: 163,830

[22] Filed: Jun. 27, 1980

[30] Foreign Application Priority Data

Jun. 28, 1979 [HU] Hungary ................................ RI 718

[51] Int. Cl.³ ..................... A61K 37/00; C07C 103/52
[52] U.S. Cl. ............................... 424/177; 260/112.5 R; 260/112.5 TR
[58] Field of Search ............... 260/112.5 TR; 424/177

[56] References Cited

U.S. PATENT DOCUMENTS 3,959,248  5/1976  Veber et al. ............... 260/112.5 TR
4,100,152  7/9178  Fujino et al. ............... 260/112.5 TR

OTHER PUBLICATIONS

Bowers, et al., Biochem. & Biophys. Res. Commun. 40, (1970), 683–691.
Chang, et al., Journal of Medicinal Chem., (1971), 14, 484–487.
Pettit, "Synthetic Peptides", vol. 4, 1976, pp. 170–171.

*Primary Examiner*—Delbert R. Phillips
*Attorney, Agent, or Firm*—Keil & Witherspoon

[57] ABSTRACT

The invention relates to new peptide derivatives which act on the central nervous system and correspond to the general formula (I), $$X-Y-W-NH_2 \qquad (I)$$

wherein
X is L-pyroglutamyl, D-pyroglutamyl, L-2-keto-imidazolidine-4-carbonyl, L-6-keto-pipecolyl, L-thiazolidine-4-carbonyl, L-prolyl or orotyl group,
Y is L-leucyl, L-norvalyl or L-histidyl group, and
W is L-prolyl, D-prolyl, L-thiazolidine-4-carbonyl, L-pipecolyl, L-homoprolyl, L-leucyl, L-isoleucyl, L-methionyl or D-pipecolyl group, or the W-NH$_2$ group stands for pyrrolidyl or piperidyl group, with the proviso that if X is L-pyroglutamyl and Y is L-histidyl group, W is other than L-prolyl group, and pharmaceutically acceptable complexes thereof.

These compounds are prepared by methods commonly applied in the peptide chemistry.

11 Claims, No Drawings

TRIPEPTIDES ACTING ON THE CENTRAL NERVOUS SYSTEM AND A PROCESS FOR THE PREPARATION THEREOF

The invention relates to new tripeptides which act on the central nervous system and pharmaceutical compositions containing the same, as well as to a process for the preparation thereof.

The new compounds according to the invention correspond to the general formula (I), $$X-Y-W-NH_2 \qquad (I)$$

wherein
X is L-pyroglutamyl, D-pyroglutamyl, L-2-keto-imidazolidine-4-carbonyl, L-6-keto-pipecolyl, L-thiazolidine-4-carbonyl, L-prolyl or orotyl group,
Y is L-leucyl, L-norvalyl or L-histidyl group, and
W is L-prolyl, D-prolyl, L-thiazolidine-4-carbonyl, L-homoprolyl, L-leucyl, L-isoleucyl, L-methionyl, L-pipecolyl or D-pipecolyl group, or
the W-NH$_2$ group stands for pyrrolidyl or piperidyl group, with the proviso that if X is L-pyroglutamyl and Y is L-histidyl group, W is other than L-prolyl group.

The pharmaceutically acceptable complexes of these compounds also fall within the scope of the invention.

The new tripeptide derivatives of the general formula (I) are structural analogues of L-pyroglutamyl-L-histidyl-L-prolinamide (Glp-His-Pro-NH$_2$) also known as "thyrotropin-releasing hormone" (TRH), in which some of the amino acid groups are replaced by other amino acid groups defined above, and optionally a pyrrolidyl or piperidyl group stands for the —W—NH$_2$ moiety.

The existence of TRH was already known in the sixties, but its structure was elucidated only in 1969 by R. Guillemin et al., and independent researches conducted by A. Schally et al. in 1970 confirmed this structure (see C. Y. Bowers et al., Endocrinology 86, 1143/1970/; R. Burgus et al., C. R. Acad. Sci./Paris/269, 1870/1969/).

The tripeptide TRH was described originally as a factor which regulates the liberation of thyrotropin (TSH) in the hypophysis of mammals. Subsequent research has revealed, however, that the biological function of this tripeptide is not restricted to the regulation of thyrotropin release, it acts on the central nervous system (CNS) as well, and this recognition opened a new field of investigations (see N. P. Plotnikoff et al., Science 178, 417/1972/; A. J. Prange et al., Lancet 2, 999/1972/). Thus, it was soon discovered that TRH, beside its hormonal function, considerably decreases the duration of sleeping caused by barbiturates and alcohol, suppresses the hypothermy provoked by various pharmaceuticals and increases the locomotive activity. An additional important factor of the CNS effects of TRH is the inhibition of catalepsy provoked by Haloperidol. There appeared a demand in the therapeutical practice for TRH analogues which exert only a weak effect on the hypophysis but act on the central nervous system to the same or even higher degree than TRH. The compounds listed in the published German patent applications Nos. 2,343,035, 2,343,037, 2,449,167, 2,514,381, 2,609,154 and 2,639,393 and in the Belgian Pat. No. 819,198 were synthetized with this aim. This extensive research work, the results and experiences of which were reviewed by A. J. Prangle et al. ("The Role of Hormones in Depression", Life Sciences 20, 1305/1977/) and A. V. Schally et al. ("Hypothalamic Regulatory Hormones", Ann. Rev. Biochem. 47, 89/1978/) has not led, however, to results satisfying the demands of therapy in all respects.

Now it has been found that when systematically replacing the individual amino acids of the tripeptide TRH by other amino acids new compounds are obtained which do not show the hormonal effect characteristic of TRH or have only minimum hormonal effects, whereas the CNS effects are retained or increased, sometimes to a considerable extent. In this respect the compounds in which a straight-chained or branched aliphatic amino acid group is substituted for His in position 2 are of particular importance. In order to attain even more selective biological effects, it appeared to be advantageous to replace the pyroglutamyl ring system of the molecule by a 6-keto-pipecolic acid group.

The tripeptides of the general formula (I) are prepared from the respective amino acids or amino acid derivatives by conventional methods of the peptide chemistry, preferably so that (a) using a compound of the general formula (II)

$$W-NH_2 \qquad (II)$$

as starting substance, wherein W is as defined above, the molecule of the required tripeptide is built up stepwise, by means of coupling methods commonly applied in the peptide chemistry, preferably utilizing activated esters, mixed anhydrides or dicyclohexyl carbodiimide, or (b) a compound of the general formula (II), $$W-NH_2 \qquad (II)$$

wherein W is as defined above, is acylated with an azide prepared from a dipeptide hydrazide of the general formula (III), $$Z-X-Y-NH-NH_2 \qquad (III)$$

wherein Z stands for benzyloxycarbonyl and X and Y are as defined above, and the Z protecting group of a compound of the general formula (IV) obtained by any of the above methods, $$Z-X-Y-W-NH_2 \qquad (IV)$$

wherein Z, X, Y and W are as defined above, is split off (preferably by catalytic hydrogenation), and the resulting compound of the general formula (I) is separated from the reaction mixture and/or optionally converted into a pharmaceutically acceptable complex.

When the tripeptide is built up stepwise, the compound of the general formula W—NH$_2$, applied preferably in excess, is reacted with an activated derivative, particularly with the pentafluorophenyl ester, of a protected amino acid of the general formula BOC—Y—OH, wherein BOC stands for tert.-butoxycarbonyl group. In this reaction the respective dipeptide derivative of the general formula BOC—Y—W—NH$_2$ is obtained in an extremely short time (some minutes). The reaction mixture can be processed very easily, and the resulting product is generally sufficiently pure for utilizing it directly in the next step.

The same dipeptide derivatives of the general formula BOC—Y—W—NH$_2$ can also be prepared, however, by other coupling methods, such as utilizing a mixed anhydride or a free acid in the presence of dicyclohexyl carbodiimide.

The resulting dipeptide derivative of the general formula BOC—Y—W—NH$_2$ is subjected to acidolysis to obtain the free dipeptide of the general formula H—Y—W—NH$_2$, and this latter compound is then reacted preferably also with the pentafluorophenyl ester of a protected amino acid of the general formula Z—X—OH, to obtain the respective protected tripeptide derivative of the general formula Z—X—Y—W—NH$_2$ in a very advantageous manner.

The method in which the starting substance of the general formula W—NH$_2$ is acylated with an azide prepared from a dipeptide hydrazide of the general formula Z—X—Y—NH—NH$_2$ has the advantage that the repective hydrazide intermediates are easy to crystallize, thus they can be isolated in very high purity.

The compounds of the general formula (I) wherein X stands for a pyroglutamyl group can also be prepared in such a way that the pyroglutamine ring is formed only in the last step of the synthesis. In this instance glutamine is introduced into the molecule as third amino acid, and the resulting tripeptide of the general formula Gln—Y—W—NH$_2$ is heated in acetic acid for some minutes.

The protected tripeptide derivatives of the general formula Z—X—Y—W—NH$_2$, obtained by any of the methods described above, can be converted into the corresponding free tripeptides of the general formula (I) preferably by catalytic hydrogenation. The resulting end-products can be purified by simple recrystallization or reprecipitation, and column chromatographic purification can also be applied, if necessary.

The pharmacological effects of the tripeptide derivatives of the general formula (I) were tested by the following biological methods:

(1) Inhibition of Haloperidol-induced catalepsy on rats (see J. Delay and P. Deniker: Compt. Rend. Congr. Med. Alenistes Neurologistes, 19, 497, Luxembourg, 1952)

The tests were performed on male Wistar rats weighing 160 to 180 g.

40 mg/kg of 4-(p-chlorophenyl)-1-(3-/p-fluorobenzoyl/-propyl)-piperidin-4-ol (Haloperidol) were administered subcutaneously into the animals, and 120 minutes after this treatment the animals were checked for the appearance of catalepsy. The rats were divided into groups of 10 animals each, and treated intravenously with TRH or the new TRH analogues. The animals belonging to the control group received physiological saline. The catalepsy-suspending effects of the individual compounds were determined 15, 30, 60, 90 and 120 minutes after the treatment. The animals that had not changed their position for 30 seconds after placing their fore-paw onto a 7 cm high column were regarded as cataleptic.

The animals showing no sign of catalepsy were counted, and the ED$_{50}$ values of the compounds were calculated from these data by probit analysis.

(2) Potentiation of locomotive activity induced on mice by L-Dopa (see The Thyroid Axis, Drugs and Behavior, p. 116, A. J. Prage Jr., Raven Press, New York, 1974)

The tests were performed on groups of 15 male mice each, weighing 18 to 22 g.

First, the animals were treated intraperitoneally with 40 mg/kg of N-methyl-N-propargyl-benzylamine (Pargyline), and then an intraperitoneal dosage of 20 mg/kg of TRH or a TRH-analogue was introduced, followed by an intraperitoneal dosage of 100 mg/kg of L-Dopa. The locomotive activity of the animals was recorded 30, 60 and 90 minutes after this treatment, and the level of potentiation was expressed in percents related to the results observed with TRH. The data are listed in Table 1.

(3) Reserpine hypothermy-reversing effect on mice (see B. M. Askew: Life Sci. 2, 725-730/1963/)

The tests were performed on groups of 10 male mice each, weighing 18 to 22 g. Reserpine was administered into the animals in an intraperitoneal dosage of 5 mg/kg, and 16 hours later the animals were treated with 20 mg/kg of TRH or a tripeptide under examination.

The rectal temperature of the animals was measured prior to the administration of reserpine (marked by "norm." in Table 1), 16 hours after the administration of reserpine (marked by "res." in Table 1), furthermore 1 and 2 hours after the administration of the tripeptide (marked by "obs.time" in Table 1). The data listed in Table 1 are the averages of the temperatures observed on the 10 animals.

(4) Influencing the duration of sleeping caused by hexobarbital

The tests were performed on groups of 10 male mice each. The animals were treated intravenously with 60 mg/kg of hexobarbital sodium (Evipan ®; Bayer), and 10 minutes later 20 mg/kg of TRH or a tripeptide under examination were administered intraperitoneally into the animals. The sleeping times of the animals were recorded, averages were calculated for the individual groups, and the results were expressed as percents related to the control group. The results are listed in Table 1.

(5) Ethanol narcosis (see J. M. Cott et al.: J. Pharm. Exp. Ther. 196, 594/1976/)

The tests were performed on groups of 20 CFLP (LATI) mice of both sexes, each weighing 18 to 22 g. 4.5 g of ethanol were introduced intraperitoneally into the animals, and 10 minutes later the animals were treated intraperitoneally with 20 mg/kg of the tripeptide under examination. The sleeping periods of the animals were recorded, averages were calculated for the individual groups, and the results were expressed as percents related to the control group. The results are listed in Table 1.

(6) Hormonal activity (TSH effect) on rats

The tests were performed on groups of 7 or 8 male Wistar rats each, weighing 200 g. The animals were treated intravenously with 20 mg/kg of TRH or a tripeptide under examination. The TSH reaction of the animals was evaluated 15 minutes after this treatment, by subjecting the blood plasma to radioimmune assay. The relative activities were calculated by the four-point method using a TPA 101 computer, and the activity of TRH was regarded as 100%.

The biological activity data of the compounds of the general formula (I) of higher interest, determined by the above tests, are listed in Table 1.

TABLE 1

| X—Y—Z—NH₂ | | | Inhibition of Haloperidol catalepsy | | Potentiation of the locomotive effect of L-Dopa, % after | | | Reserpine hypothermy reversing effect Rectal temperature, °C. | | | | Decrease of sleeping period (% related to the control animals) | | TSH effect |
|---|---|---|---|---|---|---|---|---|---|---|---|---|---|---|
| | | | $ED_{50}$ | time | | | | | | obs. time | | | | |
| X | Y | Z | mg/kg | min. | 30' | 60' | 90' | norm. | res. | 1 h | 2 h | Hexobarb. | Ethanol | |
| Kpc | Leu | Pro | 23.5 | 60 | 319 | 80 | 127 | 36.3 | 24.5 | 32.0 | 33.9 | 37 | 79 | 2.7 |
| Kpc | Nva | Pro | 10.6 | 30 | 36 | 45 | 65 | 36.3 | 23.9 | 33.1 | 32.5 | 51 | 46 | 0 |
| Glp | Leu | Tca | 31.4 | 120 | 171 | 142 | 52 | 36.2 | 24.9 | 33.1 | 32.2 | 39 | 58 | 0 |
| Glp | Leu | Pip | 38.5 | 120 | 201 | 89 | 112 | 36.4 | 24.6 | 30.7 | 31.0 | 38 | 60 | 7.2 |
| Glp | Nva | Tca | 56 | 30 | 195 | 147 | 79 | 36.5 | 23.8 | 31.4 | 30.7 | 69 | 51 | 0 |
| Kpc | Nva | Tca | 60.3 | 30 | 103 | 38 | 70 | 36.4 | 23.6 | 30.4 | 29.0 | 61 | 48 | — |
| Kpc | Nva | HPro | 35.3 | 15 | 63 | 30 | 108 | 36.3 | 20.7 | 26.5 | 32.2 | 76 | 35 | — |
| D-Glp | Leu | Pro | 70 | 15 | 54 | 58 | 115 | 36.5 | 27.4 | 25.8 | 25.6 | 97 | 54 | 0 |
| Kic | Leu | Pro | 80 | 30 | 118 | 70 | 98 | 35.5 | 24.1 | 27.7 | 28.8 | 59 | 69 | 0 |
| | TRH | | 80 | 15 | 100 | 100 | 100 | 36.2 | 25.9 | 35.5 | 30.2 | 56 | 35 | 100 |

Duration of hexobarbital-induced sleeping: ($\overline{X} \pm SE$) = 38.4 ± 1.36 min.
Duration of ethanol-induced sleeping: ($\overline{X} \pm SE$) = 46.9 ± 2.17 min.

The data of Table 1 indicate that the new analogues of TRH, in which two or three of the amino acids of the TRH molecule are replaced by other amino acids, exert considerable effects on the central nervous system. In this respect those compounds are particularly preferred in which a straight-chained or branched aliphatic amino acid group is substituted for His in position 2 of the TRH molecule. TRH analogues in which the Glp group is replaced by 6-keto-pipecolic acid are equally preferred from the same aspect. These derivatives show a minimum hormonal effect, if any, characteristic of TRH, whereas the effects exerted on the central nervous system are much higher, sometimes eight times exceeding that of TRH.

The new tripeptides according to the invention as well as their pharmaceutically acceptable salts or complexes can be applied in the therapy in the form of conventional pharmaceutical compositions. These pharmaceutical compositions contain the active agents according to the invention in combination with mineral or organic carriers suitable for enteral or paremteral administration. The pharmaceutical compositions can be presented e.g. in the form of tablets, coated tablets, injections, freeze-dried compositions, etc., and can be prepared by methods well known in the pharmaceutical industry.

The invention is elucidated in detail by the aid of the following non-limiting Examples. The abbreviations used in the examples are those commonly applied in peptide chemistry (see J. Biol. Chem. 247, 977/1972/). The additional abbreviations appearing in the examples have the following meanings:
HPro—L-homoproline
Kic—L-2-keto-imidazolidine-4-carboxylic acid
Kpc—L-6-keto-pipecolic acid
Oro—orotic acid
Pip—L-pipecolic acid
Tca—L-thiazolidine-4-carboxylic acid
DCC—dicyclohexyl carbodiimide
DCU—dicyclohexyl urea
PFPOH—pentafluorophenol
DMFA—dimethyl formamide The melting points given in the examples were determined on a Dr.Tottoli-type (Büchi) apparatus. The optical rotations were measured on a Perkin-Elmer 141 type polarimeter. When thin layer chromatography was used for identification or separation, chromatographic silica gel plates of "Kieselgel G nach Stahl" quality (E. Merck, Darmstadt) were applied as adsorbent, and the following solvent mixtures were utilized to develop the chromatograms:
(1) chloroform: methanol 9:1
(2) ethyl acetate: (pyridine:acetic acid:water 20:6:11) 95:5
(3) ethyl acetate: (pyridine:acetic acid:water 20:6:11) 9:1
(4) ethyl acetate: (pyridine:acetic acid:water 20:6:11) 8:2
(5) ethyl acetate: (pyridine:acetic acid:water 20:6:11) 3:2
(6) ethyl acetate: (pyridine:acetic acid:water 20:6:11) 2:3

The spots were developed with ninhydrin solution. The plates were dried at 105° C. for about 5 minutes after spraying, thereafter the chromatograms were exposed to chlorine gas, then, after aeration, treated with o-toluidine-potassium iodide solution.

When column chromatography was applied to separate the substances, "Kieselgel G" grade silica gel (E. Merck) with a particle size of 0.062 to 0.2 mm was utilized as adsorbent.

The solutions were evaporated under reduced pressure in a "Rotavapor R" (Büchi) apparatus at temperatures not exceeding 50° C.

The pentafluorophenyl esters of the BOC-protected amino acids were prepared according to the method of L. Kisfaludy et al. (Ann. 1973, 1421).

EXAMPLE 1

L-Pyroglutamyl-L-leucyl-L-pipecolic amide

Step 1: L-Leucyl-L-pipecolic amide hydrochloride 1.54 g (12 mmoles) of H-Pip-NH₂ are suspended in 20 ml of DMFA, and 5.16 g (13 mmoles) of BOC-Leu-OPFP and 1.68 ml (12 mmoles) of triethylamine are added to the suspension with stirring. The mixture is stirred for 6 hours, thereafter the resulting solution is evaporated in vacuo, and the oily residue is dissolved in 60 ml of chloroform. 0.2 ml of 2-dimethylaminoethylamine are added to the solution, the mixture is allowed to stand for 5 minutes, and then it is shaken thrice with 20 ml of n hydrochloric acid, each, thrice with 20 ml of n sodium hydrocarbonate solution, each, and finally with 20 ml of water. The organic phase is dried over anhydrous sodium sulfate and then evaporated. The oily residue is dissolved in 3 ml of ethyl acetate, and 10 ml of a 5 n hydrochloric acid solution in ethyl acetate are added. After one hour of standing the reaction mixture is diluted with ether, the separated precipitate is filtered off, and dried in vacuo over anhydrous sodium hydroxide. 3.13 g (94%, calculated for H-Pip-NH₂) of H-Leu-Pip-NH₂.HCl are obtained; $R_f^5 = 0.46$.

Step 2: Benzyloxycarbonyl-L-pyroglutamyl-L-leucyl-L-pipecolic amide 3.13 g (11.2 mmoles) of H-Leu-Pip-NH$_2$.HCl and 4.94 g (11.5 mmoles) of Z-Glp-OPFP are dissolved in 35 ml of DMFA, and 1.57 ml (11.2 mmoles) of triethylamine are added to the solution. After 5 minutes of stirring further 1.57 ml (11.2 mmoles) of triethylamine are added to the reaction mixture, stirring is continued for additional 20 minutes, and then the mixture is evaporated in vacuo. The residue is dissolved in 90 ml of chloroform, the solution is washed twice with 30 ml of n hydrochloric acid, each, thrice with 30 ml of n sodium hydrocarbonate solution, each, and finally with 30 ml of water. The organic phase is dried over anhydrous sodium sulfate and then evaporated. The amorphous residue is triturated with cold ether, the etheral phase is decanted, and the oily residue is solidified under n-hexane. The resulting 4.7 g of crude amorphous product is crystallized from a mixture of ethyl acetate and ether to obtain 3.32 g (61%) of Z-Glp-Leu-Pip-NH$_2$; m.p.: 143°–144° C., R$_f^4$=0.51, $[\alpha]_D^{25}$=−97.2° (c=1%, in acetic acid).

Analysis: calculated for C$_{25}$H$_{34}$O$_6$N$_4$ (m.wt.: 486.57): C: 61.71%, H: 7.04%, N: 11.51%; found: C: 61.67%, H: 7.05%, N: 11.40%.

Step 3: L-Pyroglutamyl-L-leucyl-L-pipecolic amide 2.1 g (4.32 mmoles) of Z-Glp-Leu-Pip-NH$_2$ are dissolved in 40 ml of methanol. 0.2 g of a 10% palladium-on-carbon catalyst are added, and hydrogen is bubbled through the mixture for one hour. The catalyst is filtered off, the filtrate is evaporated, and the residue is triturated with ether. The resulting crude product (1.48 g) is dissolved in 20 ml of water, the solution is decolourized, filtered, and 4 g of sodium chloride are dissolved in the clear filtrate. The aqueous solution is extracted thrice with 10 ml of chloroform, each. The chloroform solutions are combined, dried over anhydrous sodium sulfate, evaporated, and the amorphous residue is triturated with a mixture of ethyl acetate and ether. 1.33 g (87.5%) of Glp-Leu-Pip-NH$_2$ are obtained; R$_f^5$=0.60, $[\alpha]_D^{25}$=−86.4° (c=1%, in acetic acid).

EXAMPLE 2

L-Pyroglutamyl-L-leucyl-L-thiazolidine-4-carboxylic acid amide

Step 1: L-Leucyl-L-thiazolidine-4-carboxylic acid amide hydrochloride 1.81 g (11 mmoles) of H-Tca-NH$_2$.HCl (S. Ratner, H. T. Clarke, J. Am. Chem. Soc. 59, 200 /1937/) are suspended in 30 ml of DMFA, and 3.97 g (10 mmoles) of BOC-Leu-OPFP, 1.49 g (11 mmoles) of 1-hydroxybenzotriazole and 1.22 ml (11 mmoles) of N-methylmorpholine are added to the suspension. The resulting solution is allowed to stand at room temperature overnight, thereafter it is evaporated in vacuo, and the residue is dissolved in 80 ml of chloroform. The chloroform solution is washed thrice with 20 ml of n hydrochloric acid, each, thrice with 20 ml of n sodium hydrocarbonate solution, each, and finally with 10 ml of water, dried over anhydrous sodium sulfate and evaporated in vacuo. The foam-like amorphous residue is dissolved in 5 ml of ethyl acetate, and 10 ml of a 7 n hydrochloric acid solution in ethyl acetate are added. After one hour of standing the reaction mixture is diluted with ether, the separated precipitate is filtered off and dried in vacuo over anhydrous sodium hydroxide. 1.84 g (65%, calculated for BOC-Leu-OPFP) of H-Leu-Tca-NH$_2$.HCl are obtained; R$_f^5$=0.25, m.p.: 170°–174° C. (decomposition).

Step 2: Benzyloxycarbonyl-L-pyroglutamyl-L-leucyl-L-thiazolidine-4-carboxylic acid amide 1.69 g (6 mmoles) of H-Leu-Tca-NH$_2$.HCl are suspended in 20 ml of DMFA, and 2.7 g (6.3 mmoles) of Z-Glp-OPFP and 0.84 ml (6 mmoles) of triethylamine are added to the suspension. The reaction mixture is stirred for 20 minutes, evaporated in vacuo, the residue is dissolved in 50 ml of chloroform, and the solution is washed twice with 10 ml of n hydrochloric acid, each, thrice with 10 ml of n sodium hydrocarbonate solution, each, and finally with 10 ml of water. The organic solution is dried over anhydrous sodium sulfate and evaporated in vacuo. The residue is triturated with ether, and the resulting 2.4 g of crude product is repeatedly precipitated from a mixture of ethyl acetate and ether. 1.64 g (56%) of Z-Glp-Leu-Tca-NH$_2$ are obtained; m.p.: 108°–110° C., R$_f^4$=0.46, $[\alpha]_D^{25}$=−130.30° (c=1%, in acetic acid).

Step 3: L-Pyroglutamyl-L-leucyl-L-thiazolidine-4-carboxylic acid amide 1.62 g (3.3 mmoles) of Z-Glp-Leu-Tca-NH$_2$ are dissolved in 6 ml of an ice-cold 3.5 n solution of hydrobromic acid in glacial acetic acid, and the solution is allowed to stand at 0°–5° C. for 1.5 hours. Thereafter the reaction mixture is diluted with ether, the diluent is decanted, and the oily residue is dissolved in 20 ml of water. The aqueous solution is neutralized with solid sodium hydrocarbonate washed thrice with 10 ml of ether, each, evaporated in vacuo, and the residue is dissolved in 20 ml of chloroform. The chloroform solution is dried over anhydrous sodium sulfate, evaporated, and the amorphous residue is triturated with ether. The resulting 1.13 g of crude product are dissolved in solvent mixture (4), the solution is applied onto a column filled with 20 g of silica gel, and the column is eluted with the same solvent mixture. The fractions which contain the pure product are combined, and the product is isolated. The resulting 0.78 g of amorphous substance are dissolved in 20 ml of water, the solution is decolourized, filtered, and the clear filtrate is freeze-dried. 0.62 g (53%) of Glp-Leu-Tca-NH$_2$ are obtained; R$_f^5$=0.53, $[\alpha]_D^{25}$=−145.0° (c=1%, in acetic acid).

EXAMPLE 3

L-Pyroglutamyl-L-leucyl-D-prolinamide

Step 1: Benzyloxycarbonyl-L-pyroglutamyl-L-leucyl-D-prolinamide 1.54 g (5.8 mmoles) of H-Leu-D-Pro-NH$_2$.HCl are dissolved in 20 ml of DMFA, and 0.81 ml (5.8 mmoles) of triethylamine and 2.58 g (6 mmoles) of Z-Glp-OPFP are added to the solution. The reaction mixture is stirred for 5 minutes, further 0.81 ml (5.8 mmoles) of triethylamine are added, stirring is continued for additional 10 minutes, and the mixture is evaporated in vacuo. The residue is dissolved in 60 ml of chloroform, and the solution is washed thrice with 15 ml of n hydrochloric acid, each, thrice with 15 ml of n sodium hydrocarbonate solution, each, and finally with 15 ml of water. The organic phase is dried over anhydrous sodium sulfate, evaporated, and the amorphous residue is triturated with ether. The resulting 2.1 g of crude product is recrystallized from 5 ml of ethyl acetate to obtain 1.8 g (66%) of Z-Glp-Leu-D-Pro-NH$_2$; m.p.: 153°–157° C., R$_f^4$=0.38, $[\alpha]_D^{25}$=−24.5° (c=1%, in acetic acid).

Step 2: L-Pyroglutamyl-L-leucyl-D-prolinamide 1.5 g (3.25 mmoles) of Z-Glp-Leu-D-Pro-NH$_2$ are dissolved in 70 ml of methanol, 0.3 g of a 10% palladium-on-carbon catalyst are added to the solution, and hydrogen is bubbled through the mixture for one hour. The catalyst is filtered off, the filtrate is evaporated, and the amorphous residue is triturated with ether. The resulting 0.94 g of crude product are dissolved in water, the solution is decolourized, filtered, and the clear filtrate is freeze-dried. 0.87 g (79%) of Glp-Leu-D-Pro-NH$_2$ are obtained; R$_f^5$=0.47, $[α]_D^{25}$= +8.4° (c=1%, in acetic acid).

EXAMPLE 4

L-Pyroglutamyl-L-norvalyl-L-thiazolidine-4-carboxylic acid amide

Step 1: L-Norvalyl-L-thiazolidine-4-carboxylic acid amide 8.0 g (20 mmoles) of BOC-Nva-OH.DCHA are suspended in 60 ml of ether, 20 ml of 2 n sulfuric acid are added, and the mixture is shaken until the solid dissolves completely. The etheral solution is separated, washed once again with 20 ml of 2 n sulfuric acid and then once with 20 ml of water, dried over anhydrous sodium sulfate and then evaporated. The oily residue is dissolved in 40 ml of DMFA, 2.8 ml (20 mmoles) of triethylamine are added to the solution, the mixture is cooled to −15° C., and 2.5 ml (20 mmoles) of pivaloyl chloride are added dropwise to the stirred mixture at such a rate that the temperature of the mixture remains below −5° C. The resulting suspension is stirred at the same temperature for 10 minutes to obtain a solution of the mixed anhydride. 3.1 ml (22 mmoles) of triethylamine are added to a suspension of 3.72 g (22 mmoles) of H-Tca-NH$_2$.HCl in 30 ml of DMFA, and the separated precipitate is filtered off. The filtrate is added dropwise to the above solution of the mixed anhydride at a temperature below −5° C. After the addition the mixture is stirred at −10° C. for 30 minutes, allowed to stand in a refrigerator overnight, and then evaporated in vacuo. The residue is dissolved in 100 ml of chloroform, the solution is washed thrice with 20 ml of n hydrochloric acid, each, thrice with 20 ml of n sodium hydrocarbonate solution, each, and finally with 20 ml of water, dried over anhydrous sodium sulfate, and then evaporated. The oily residue is dissolved in 20 ml of ethyl acetate, the solution is cooled to a temperature below 5° C., and 20 ml of a 5 n hydrochloric acid solution in ethyl acetate are added. The reaction mixture is maintained in an ice bath for one hour, thereafter it is diluted with ether, the separated precipitate is filtered off and dried in vacuo over anhydrous sodium hydroxide. 3.77 g (70%, calculated for BOC-Nva-OH. DCHA) of H-Nva-Tca-NH$_2$.HCl are obtained; R$_f^5$=0.20.

Step 2: Benzyloxycarbonyl-L-pyroglutamyl-L-norvalyl-L-thiazolidine-4-carboxylic acid amide 2.8 g (10.5 mmoles) of H-Nva-Tca-NH$_2$.HCl are suspended in 50 ml of DMFA, and 1.47 ml (10.5 mmoles) of triethylamine and 5.15 g (12 mmoles) of Z-Glp-OPFP are added to the stirred suspension. After 5 minutes further 1.47 ml (10.5 mmoles) of triethylamine are added, the reaction mixture is stirred for additional 10 minutes, and then evaporated in vacuo. The residue is dissolved in 100 ml of chloroform, and the solution is washed thrice with 20 ml of n hydrochloric acid, each, thrice with 20 ml of n sodium hydrocarbonate solution, each, and finally with 20 ml of water. The organic solution is dried over anhydrous sodium sulfate and evaporated. The amorphous residue is triturated with ether, and the resulting 4.6 g of crude product is recrystallized from a mixture of ethyl acetate and ether. 3.2 g (64%) of Z-Glp-Nva-Tca-NH$_2$ are obtained; m.p.: 116°–118° C., R$_f^4$=0.45, $[α]_D^{25}$= −129.0° (c=1%, in acetic acid).

Step 3: L-Pyroglutamyl-L-norvalyl-L-thiazolidine-4-carboxylic acid amide 4.76 g (10 mmoles) of Z-Glp-Nva-Tca-NH$_2$ are dissolved in 20 ml of an ice-cold 3.5 n solution of hydrobromic acid in glacial acetic acid, and the resulting solution is allowed to stand at 0°–5° C. for 1.5 hours. The reaction mixture is diluted with ether, and the solvent is decanted. The oily residue is dissolved in 50 ml of water, the solution is neutralized with solid sodium hydrocarbonate, washed thrice with 20 ml of ether, each, and then evaporated. The residue is dissolved in 100 ml of chloroform, the solution is dried over anhydrous sodium sulfate, evaporated, and the amorphous residue is triturated with ether. The resulting 3 g of crude product are applied onto a column filled with 80 g of silica gel, and the column is eluted with solvent mixture (4). The fractions which contain the pure product are combined, and the product is isolated. The resulting 2.18 g of amorphous substance are dissolved in 40 ml of water, the solution is decolourized, filtered, and the filtrate is freeze-dried. 1.84 g (54%) of Glp-Nva-Tca-NH$_2$ are obtained; R$_f^5$=0.50, $[α]_D^{25}$= −145.6° (c=1%, in acetic acid).

EXAMPLE 5

L-Pyroglutamyl-L-norvalyl-L-leucinamide

Step 1: tert.-Butoxycarbonyl-L-norvalyl-L-leucine methyl ester

BOC-Nva-OH, liberated from 8.0 g (20 mmoles) of the DCHA salt as described in Step 1 of Example 4, and 3.82 g (21 mmoles) of H-Leu-OMe.HCl are dissolved in 60 ml of chloroform, and 2.94 ml (21 mmoles) of triethylamine are added. The solution is cooled with ice, and a solution of 4.33 g (21 mmoles) of DCC in 40 ml of chloroform is added with stirring. The reaction mixture is allowed to stand at 5° C. overnight, the separated DCU is removed by filtration, the filtrate is washed thrice with 30 ml of n hydrochloric acid, each, thrice with 30 ml of n sodium hydrocarbonate solution, each, and finally with 30 ml of water, dried over anhydrous sodium sulfate, and then evaporated. The crystalline residue is triturated with n-hexane, filtered off, and the resulting 6.65 g of crude product is recrystallized from a mixture of 5 ml of ethyl acetate and 20 ml of petroleum ether. 5.20 g (75%) of BOC-Nva-Leu-OMe are obtained; m.p.: 100°–101° C., R$_f^2$=0.84, $[α]_D^{25}$= −47.5° (c=1%, in methanol).

Step 2: tert.-Butoxycarbonyl-L-norvalyl-L-leucinamide 5.0 g (14.5 mmoles) of BOC-Nva-Leu-OMe are dissolved in 50 ml of methanol, and gaseous ammonia is introduced into the solution for 0.5 hours under ice cooling. The solution is allowed to stand at room temperature overnight, then cooled again, saturated with gaseous ammonia, and evaporated after 4 hours of standing. The crystalline residue is recrystallized from a mixture of ethyl acetate and ether. 4.37 g (91%) of BOC-Nva-Leu-NH$_2$ are obtained; m.p.: 158°–159° C., R$_f^2$=0.60, $[α]_D^{25}$= −48.7° (c=1%, in methanol).

Step 3: L-Norvalyl-L-leucinamide hydrochloride 4.12 g (12.5 mmoles) of BOC-Nva-Leu-NH$_2$ are suspended in 15 ml of ethyl acetate, and 20 ml of a 6 n hydrochloric acid solution in ethyl acetate are added to the suspension. After one hour of standing the reaction mixture is diluted with ether, the separated precipitate is filtered off, and the resulting 3.64 g of crude product is recrystallized from 25 ml of methanol. 2.75 g (83%) of H-Nva-Leu-NH$_2$.HCl are obtained; m.p.: 215°–216° C., R$_f^5$=0.45, [α]$_D^{25}$=−3.47° (c=1%, in methanol).

Step 4: Benzyloxycarbonyl-L-pyroglutamyl-L-norvalyl-L-leucinamide 2.67 g (10 mmoles) of H-Nva-Leu-NH$_2$.HCl are dissolved in 30 ml of DMFA, and 1.4 ml (10 mmoles) of triethylamine are added. The separated precipitate is filtered off, and 4.72 g (11 mmoles) of Z-Glp-OPFP are added to the filtrate. After 5 minutes further 1.4 ml (10 mmoles) of triethylamine are added to the mixture, and after 10 minutes the mixture is evaporated in vacuo. The residue is triturated with ether, and the resulting 5.5 g of crude product are recrystallized from ethanol. 3.84 g (81%) of Z-Glp-Nva-Leu-NH$_2$ are obtained; m.p.: 241°–242° C., R$_f^4$=0.55, [α]$_D^{25}$=−62.6° (c=1%, in acetic acid).

Step 5: L-Pyroglutamyl-L-norvalyl-L-leucinamide 3.8 g (8 mmoles) of Z-Glp-Nva-Lue-NH$_2$ are dissolved in 200 ml of acetic acid, 0.8 g of a 10% palladium-on-carbon catalyst are added, and hydrogen is bubbled through the mixture for one hour. The catalyst is filtered off, and the gelly residue is triturated with ether. 2.7 g (99%) of Glp-Nva-Leu-NH$_2$ are obtained; m.p.: 240° C. (decomposition), R$_f^5$=0.57, [α]$_D^{25}$=−55.8° (c=1%, in acetic acid).

EXAMPLE 6

L-Pyroglutamyl-L-norvalyl-L-isoleucinamide

Step 1: tert.-Butoxycarbonyl-L-norvalyl-L-isoleucinamide 3.7 g (19 mmoles) of H-Ile-NH$_2$.HCl are dissolved in ml of DMFA, and 2.7 ml (19 mmoles) of triethylamine and 6.63 g (17.3 mmoles) of BOC-Nva-OPFP are added to the solution with stirring. After 5 minutes further 2.4 ml (17.3 mmoles) of triethylamine are added to the mixture, the mixture is stirred for additional 10 minutes, and then evaporated in vacuo. The residue is dissolved in 100 ml of chloroform. The solution is washed twice with 20 ml of n hydrochloric acid, each, thrice with 20 ml of n sodium hydrocarbonate solution, each, and then with 20 ml of water, dried over anhydrous sodium sulfate and evaporated. The crystalline residue is triturated with ether to obtain 4.7 g (83%) of BOC-Nva-Ile-NH$_2$; m.p.: 192°–194° C., R$_f^2$=0.60, [α]$_D^{25}$=−43.7° (c=1%, in methanol).

Step 2: L-Norvalyl-L-isoleucinamide hydrochloride 4.5 g (13.7 mmoles) of BOC-Nva-Ile-NH$_2$ are suspended in 20 ml of ethyl acetate, and 12 ml of a 6 n hydrochloric acid solution in ethyl acetate are added to the suspension. After one hour of standing the reaction mixture is diluted with ether, and the separated precipitate is filtered off. The resulting 3.6 g of crude product are recrystallized from a mixture of methanol and ether to obtain 3.5 g (96%) of H-Nva-Ile-NH$_2$.HCl; m.p.: 254°–255° C., R$_f^5$=0.45, [α]$_D^{25}$=+3.8° (c=1%, in methanol).

Step 3: Benzyloxycarbonyl-L-pyroglutamyl-L-norvalyl-L-isoleucinamide 3.3 g (12.4 mmoles) of H-Nva-Ile-NH$_2$.HCl are dissolved in 40 ml of DMFA, and 1.74 ml (12.4 mmoles) of triethylamine and 5.85 g (13.6 mmoles) of Z-Glp-OPFP are added to the solution with stirring. After 5 minutes further 1.74 ml (12.4 mmoles) of triethylamine are added to the mixture, whereupon the mixture gellifies in some seconds. The gel is diluted with ether, the resulting mixture is stored in a refrigerator for 2 hours, and then filtered. 5.1 g (86%) of Z-Glp-Nva-Ile-NH$_2$ are obtained; m.p.: 252°–253° C., R$_f^4$=0.60, [α]$_D^{25}$=−57.5° (c=1%, in acetic acid).

Step 4: L-Pyroglutamyl-L-norvalyl-L-isoleucinamide 4.75 g (10 mmoles) of Z-Glp-Nva-Ile-NH$_2$ are dissolved in 200 ml of acetic acid, 1 g of a 10% palladium-on-carbon catalyst is added, and hydrogen is bubbled through the mixture for one hour. The catalyst is filtered off, the filtrate is evaporated, and the residue is triturated with ether. 3.34 g (98%) of Glp-Nva-Ile-NH$_2$ are obtained; m.p.: 267°–270° C. (decomposition), R$_f^5$=0.61, [α]$_D^{25}$=−50.2° (c=1%, in acetic acid).

EXAMPLE 7

L-Pyroglutamyl-L-norvalyl-L-methioninamide

Step 1: tert.-Butoxycarbonyl-L-norvalyl-L-methionine methyl ester

BOC-Nva-OH, liberated from 4.78 g (12 mmoles) of the DCHA salt as described in Step 1 of Example 4, and 2.6 g (13 mmoles) of H-Met-OMe.HCl are dissolved in 40 ml of chloroform, and 1.82 ml (13 mmoles) of triethylamine are added. The mixture is cooled with ice, and a solution of 2.58 g (12.5 mmoles) of DCC in 20 ml of chloroform is added under stirring. The reaction mixture is allowed to stand at 5° C. overnight, thereafter the separated DCU is filtered off. The filtrate is washed thrice with 20 ml of n hydrochloric acid, each, thrice with 20 ml of n sodium hydrocarbonate solution, each, and then with 20 ml of water, dried over anhydrous sodium sulfate, and evaporated. The oily residue is crystallized from petroleum ether, and the resulting 3.42 g of crude product is recrystallized from a mixture of ethyl acetate and petroleum ether. 3.08 g (71%) of BOC-Nva-Met-OMe are obtained; m.p.: 69°–70° C., R$_f^2$=0.81, [α]$_D^{25}$=−42.7° (c=1%, in methanol).

Step 2: tert.-Butoxycarbonyl-L-norvalyl-L-methioninamide 1.81 g (5 mmoles) of BOC-Nva-Met-OMe are dissolved in 20 ml of methanol, and gaseous ammonia is introduced into the solution for 0.5 hours under ice cooling. The reaction mixture is allowed to stand at room temperature overnight, and then stored in a cold place for some hours. The separated crystalline product is filtered off to obtain 1.27 g of the desired product. The filtrate is evaporated, and the residue is recrystallized from 5 ml of ethanol to obtain further 0.35 g of the product. Thus 1.62 g (93%) of BOC-Nva-Met-NH$_2$ are obtained; m.p.: 166°–167° C., R$_f^2$=0.57, [α]$_D^{25}$=−40.9° (c=1%, in methanol).

Step 3: L-Norvalyl-L-methioninamide hydrochloride 4.5 g (13 mmoles) of BOC-Nva-Met-NH$_2$ are suspended in 20 ml of ethyl acetate, and 20 ml of a 6 n hydrochloric acid solution in ethyl acetate are added to the suspension. After one hour of standing the reaction mixture is diluted with ether, the separated precipitate is filtered off, and dried in vacuo over anhydrous sodium hydroxide. The resulting 4 g of crude product are recrystallized from a mixture of methanol and ether. 3.28 g (89%) of H-Nva-Met-NH$_2$.HCl are obtained; m.p.: 198°–200° C., R$_f^5$=0.40, [α]$_D^{25}$=+10.2° (c=1%, in methanol).

Step 4: tert.-Butoxycarbonyl-L-glutaminyl-L-norvalyl-L-methioninamide 2.84 g (10 mmoles) of H-Nva-Met-NH$_2$.HCl are suspended in 40 ml of DMFA, and 1.4 ml (10 mmoles) of triethylamine and 4.53 g (11 mmoles) of BOC-Gln-OPFP are added to the suspension with stirring. After 5 minutes further 1.4 ml (10 mmoles) of triethylamine are added to the mixture, and after an additional stirring of 10 minutes the thick suspension is evaporated in vacuo. The solid residue is triturated with ethanol to obtain 4.82 g of crude product. This substance is admixed with 50 ml of ethanol, the mixture is heated to boiling, cooled, and the resulting suspension is stored at a cool place for some hours. The precipitate is filtered off to obtain 4.08 g (86%) of BOC-Gln-Nva-Met-NH$_2$; m.p.: 237°–238° C., $R_f^4$=0.43, $[\alpha]_D^{25}$=−37.1° (c=1%, in acetic acid).

Step 5: L-Pyroglutamyl-L-norvalyl-L-methioninamide 3.8 g (8 mmoles) of BOC-Gln-Nva-Met-NH$_2$ are dissolved in 100 ml of a 98% formic acid, the solution is allowed to stand at room temperature for 2 hours, and then evaporated in vacuo. The oily residue is dissolved in 50 ml of acetic acid, the solution is boiled for 2 minutes, and then evaporated in vacuo. The gelly residue is triturated with ether to obtain 2.8 g (98%) of Glp-Nva-Met-NH$_2$; m.p.: 249°–250° C. (decomposition), $R_f^5$=0.58, $[\alpha]_D^{25}$=−48.4° (c=1%, in acetic acid).

EXAMPLE 8

N-(L-Pyroglutamyl-L-leucyl)-pyrrolidine

Step 1: N-(L-Leucyl)-pyrrolidine hydrochloride 3.46 g (15 mmoles) of BOC-Leu-OH are dissolved in 50 ml of ethyl acetate, 2.1 ml (15 mmoles) of triethylamine are added, and the mixture is cooled to −15° C. 1.97 ml (16 mmoles) of pivaloyl chloride are added dropwise to the stirred mixture at such a rate that the temperature remains below −10° C., the resulting suspension is stirred for 10 minutes, and then 1.37 ml (16.5 mmoles) of pyrrolidine are added dropwise to the suspension at the same temperature. When the addition is complete, the mixture is stirred at −10° C. for additional 30 minutes, and then allowed to stand at 5° C. for 3 hours. The reaction mixture is shaken thrice with 10 ml of n hydrochloric acid, each, thrice with 10 ml of n sodium hydrocarbonate solution, each, and then with 10 ml of water, dried over anhydrous sodium sulfate, and evaporated in vacuo. The oily residue is dissolved in 5 ml of ethyl acetate, and 10 ml of a 5 n hydrochloric acid solution in ethyl acetate are added. After one hour of standing the solution is diluted with ether and extracted with water. The aqueous solution is washed with ether, rendered alkaline with potassium carbonate, and then extracted with chloroform. The chloroform solution is dried over anhydrous sodium sulfate, evaporated, the oily residue is dissolved in 10 ml of ether, and the pH of the solution is adjusted to 3 with a concentrated solution of hydrochloric acid in ethyl acetate. The separated crystals are filtered off to obtain 2.41 g (73%) of H-Leu-pyrrolidine.HCl; m.p.: 170°–174° C. (decomposition), $R_f^5$=0.37.

Step 2: N-(Benzyloxycarbonyl-L-pyroglutamyl-L-leucyl)-pyrrolidine 1.7 g (7.7 mmoles) of H-Leu-pyrrolidine.HCl, 3.0 g (7 mmoles) of Z-Glp-OPFP and 1.08 ml (7.7 mmoles) of triethylamine are dissolved in 20 ml of chloroform, and after 5 minutes further 0.98 ml (7 mmoles) of triethylamine are added to the solution. The solution is allowed to stand for additional 5 minutes, thereafter it is diluted with 30 ml of chloroform, and washed twice with 10 ml of n hydrochloric acid, each, thrice with 10 ml of n sodium hydrocarbonate solution, each, and finally with 10 ml of water. The chloroform solution is dried over anhydrous sodium sulfate and evaporated. The oily residue is crystallized from n-hexane, and the resulting 2.85 g of crude product are recrystallized from a mixture of ethanol and ether. 2.14 g (71%) of Z-Glp-Leu-pyrrolidine are obtained; m.p.: 109°–110° C., $R_f^4$=0.55, $[\alpha]_D^{25}$=−53.3° (c=1%, in acetic acid).

Analysis: calculated for C$_{23}$H$_{31}$O$_5$N$_3$ (mol.wt.: 429.52): C: 64.32%, H: 7.27%, N: 9.78%; found: C: 64.31%, H: 7.47%, N: 9.78%.

Step 3: N-(Pyroglutamyl-L-leucyl)-pyrrolidine 2.0 g (4.66 mmoles) of Z-Glp-Leu-pyrrolidine are dissolved in 40 ml of methanol, 0.4 g of a 10% palladium-on-carbon catalyst are added to the solution, and hydrogen is bubbled through the mixture for one hour. The catalyst is filtered off, the filtrate is evaporated, the oily residue is dissolved in ether, and the solution is allowed to stand at a cool place overnight. The separated crystals are filtered off to obtain 1.25 g (91%) of Glp-Leu-pyrrolidine; m.p.: 103°–104° C., $R_f^5$=0.65, $[\alpha]_D^{25}$=−31.6° (c=1%, in acetic acid). Analysis for amino acids: Glu=1.00 (1.0), Leu=1.00 (1.0).

EXAMPLE 9

N-(L-Pyroglutamyl-L-leucyl)-piperidine

Step 1: N-(L-Leucyl)-piperidine hydrochloride 3.46 g (15 mmoles) of BOC-Leu-OH are dissolved in 50 ml of ethyl acetate, 2.1 ml (15 mmoles) of triethylamine are added, and the solution is cooled to −15° C. The mixture is stirred at the same temperature, and 1.97 ml (16 mmoles) of pivaloyl chloride are added dropwise, followed by 1.65 ml (16.5 mmoles) of piperidine. The mixture is stirred for 10 minutes between the introduction of the two reactants. When the addition is complete, the mixture is stirred for additional 30 minutes at −10° C., and then it is allowed to stand in a refrigerator overnight. The separated precipitate is filtered off, the filtrate is washed thrice with 10 ml of n hydrochloric acid, each, thrice with 10 ml of n sodium hydrocarbonate solution, each, and then with 10 ml of water, dried over anhydrous sodium sulfate, and evaporated. The oily residue is dissolved in 15 ml of a 4 n solution of hydrochloric acid in ethyl acetate, the mixture is allowed to stand for one hour, then it is diluted with ether and stored in a refrigerator overnight. The precipitate is filtered off to obtain 2.0 g (57%, calculated for BOC-Leu-OH) of H-Leu-piperidine.HCl; m.p.: 123°–125° C., $R_f^5$=0.45.

Step 2: N-(Benzyloxycarbonyl-L-pyroglutamyl-L-leucyl)-piperidine 1.81 g (7.7 mmoles) of H-Leu-piperidine.HCl, 3.0 g (7 mmoles) of Z-Glp-OPFP and 1.08 ml (7.7 mmoles) of triethylamine are dissolved in 20 ml of chloroform, and after 5 minutes of standing further 0.98 ml (7 mmoles) of triethylamine are added. The solution is allowed to stand for additional 5 minutes, then diluted with 30 ml of chloroform, and washed twice with 10 ml of n hydrochloric acid, each, thrice with 10 ml of n sodium hydrocarbonate solution, each, and finally with 10 ml of water. The chloroform solution is dried over anhydrous sodium sulfate and then evaporated. A crystallizing oil is obtained, which is triturated with a mixture of ether and n-hexane. The resulting 2.75 g of crude product is recrystallized from a mixture of ethanol and ether to obtain 2.21 g (71%) of Z-Glp-Leu-piperidine; m.p.: 113°–115° C., $R_f^4$=0.69, $[\alpha]_D^{25}$=−42.5° (c=1%, in acetic acid).

Analysis: calculated for C$_{24}$H$_{33}$O$_5$N$_3$ (mol.wt.: 443.55): C: 64.99%, H: 7.50%, N: 9.47%; found: C: 64.90%, H: 7.72%, N: 9.53%.

Step 3: N-(L-Pyroglutamyl-L-leucyl)-piperidine 2.0 g (4.51 mmoles) of Z-Glp-Leu-piperidine are dissolved in 40 ml of methanol, 0.4 g of a 10% palladium-on-carbon catalyst are added to the solution, and hydrogen is bubbled through the mixture for one hour. The catalyst is filtered off, the filtrate is evaporated, and the residue is crystallized from ether. 1.12 g (81%) of Glp-Leu-piperidine are obtained; m.p.: 99°–100° C., $R_f^5 = 0.71$, $[\alpha]_D^{25} = +30.4°$ (c=1%, in acetic acid). Analysis for amino acids: Glu=0.95 (1.0), Leu=1.00 (1.0).

EXAMPLE 10

L-Thiazolidine-4-carbonyl-L-leucyl-L-prolinamide

Step 1: L-Thiazolidine-4-carbonyl-L-leucyl-L-prolinamide 5.13 g (22 mmoles) of BOC-Tca-OH and 4.05 g (22 mmoles) of PFPOH are dissolved in 60 ml of ethyl acetate, and 4.12 g (20 mmoles) of DCC are added to the stirred solution under ice cooling. The reaction mixture is stirred at 0°–5° C. for 2 hours, thereafter the precipitated DCU is filtered off, and the filtrate is evaporated. The oily residue is dissolved in 50 ml of n-hexane, the solution is washed five times with 25 ml of n sodium hydrocarbonate solution, each, and twice with 25 ml of water, each, dried over anhydrous sodium sulfate, and then evaporated. The resulting 7.32 g of oily BOC-Tca-OPFP are dissolved in 20 ml of DMFA, and the solution is poured into a suspension of 5.23 g (20 mmoles) of H-Leu-Pro-NH₂.HCl in 30 ml of DMFA. 2.8 ml (20 mmoles) of triethylamine are added to the stirred mixture under ice cooling. After 5 minutes further 2.8 ml (20 mmoles) of triethylamine are introduced, the mixture is stirred for additional 20 minutes, and then evaporated in vacuo. The oily residue is dissolved in 100 ml of chloroform, the solution is shaken thrice with 30 ml of n hydrochloric acid, each, thrice with 30 ml of n sodium hydrocarbonate solution, each, and then with 30 ml of water, dried over anhydrous sodium sulfate, and evaporated to obtain 8.84 g of BOC-Tca-Leu-Pro-NH₂ as an oily residue. This substance is dissolved in 15 ml of ethyl acetate, and 15 ml of a 6 n solution of hydrochloric acid in ethyl acetate are added. After one hour of standing the reaction mixture is diluted with ethyl acetate, the separated precipitate is triturated, filtered off, and dried in vacuo over anhydrous sodium hydroxide. The resulting 8.05 g of tripeptidamide hydrochloride are dissolved in 80 ml of water, the solution is shaken thrice with 20 ml of ether, each, the pH of the aqueous phase is adjusted to 8 with sodium hydrocarbonate, and the alkaline solution is extracted five times with 20 ml of chloroform, each. The chloroform solutions are combined, dried over anhydrous sodium sulfate and evaporated. The residue is triturated with ether to obtain 5.20 g (76%) of H-Tca-Leu-Pro-NH₂; m.p.: 159°–160° C., $R_f^5=0.63$, $[\alpha]_D^{25}=-162.9°$ (c=1%, in acetic acid).

EXAMPLE 11

L-2-Ketoimidazolidine-4-carbonyl-L-leucyl-L-prolinamide

Step 1: Benzyloxycarbonyl-L-2-ketoimidazolidine-4-carboxylic acid pentafluorophenyl ester 10.56 g (40 mmoles) of Z-Kic-OH and 8.09 g (44 mmoles) of PFPOH are dissolved in 100 ml of a 1:2 mixture of DMFA and dioxane, and 9.06 g (44 mmoles) of DCC are added to the stirred solution under ice cooling. The reaction mixture is stirred at 0°–5° C. for 1.5 hours, thereafter the separated DCU is filtered off, and the filtrate is evaporated. The oily residue is crystallized from n-hexane, and the resulting 16.46 g of crude product is recrystallized from 50 ml of ethyl acetate. 12.75 g (74%) of Z-Kic-OPFP are obtained; m.p.: 146°–148° C., $R_f^1=0.53$, $[\alpha]_D^{25}=-42.1°$ (c=1%, in ethyl acetate).

Analysis: calculated for $C_{18}H_{11}O_5N_2F_5$ (mol.wt.: 430.29): C: 50.25%, H: 2.58%, N: 6.51%, F: 22.08%; found: C: 49.88%, H: 2.35%, N: 6.66%, F: 21.81%.

Step 2: Benzyloxycarbonyl-L-2-ketoimidazoline-4-carbonyl-L-leucyl-L-prolinamide 2.38 g (9 mmoles) of H-Leu-Pro-NH₂.HCl are suspended in 30 ml of DMFA, and 3.87 g (9 mmoles) of Z-Kic-OPFP and 1.26 ml (9 mmoles) of triethylamine are added to the suspension. After 5 minutes of stirring further 1.26 ml (9 mmoles) of triethylamine are added, the mixture is stirred for additional 20 minutes, and then evaporated in vacuo. The residue is dissolved in 50 ml of chloroform, the solution is shaken twice with 10 ml of n hydrochloric acid, each, and thrice with 10 ml of n sodium hydrocarbonate solution, each, dried over anhydrous sodium sulfate, and evaporated. The oily residue is crystallized from ether. The resulting 3.31 g of crude product are boiled in 30 ml of ethyl acetate, the suspension is allowed to cool for some hours, and then the solid is filtered off. 3.0 g (70%) of Z-Kic-Leu-Pro-NH₂ are obtained; m.p.: 172°–174° C., $R_f^4=0.18$, $[\alpha]_D^{25}=-102.6°$ (c=1%, in acetic acid).

Analysis: calculated for $C_{23}H_{31}O_6N_5$ (mol.wt.: 473.50): C: 58.34%, H: 6.60%, N: 14.79%; found: C: 57.52%, H: 6.62%, N: 14.62%.

Step 3: L-2-Ketoimidazolidine-4-carbonyl-L-leucyl-L-prolinamide 1.2 g (2.54 mmoles) of Z-Kic-Leu-Pro-NH₂ are dissolved in 30 ml of water, 0.25 g of a 10% palladium-on-carbon catalyst are added, and hydrogen is bubbled through the mixture for 4 hours. The catalyst is filtered off, the filtrate is evaporated, and the amorphous residue is dried in vacuo over phosphorous pentoxide. The resulting 0.75 g of crude product are dissolved in water, the solution is decolourized, filtered, and the clear filtrate is freeze-dried. 0.61 g (71%) of Kic-Leu-Pro-NH₂ are obtained; $R_f^5=0.35$, $[\alpha]_D^{25}=-90.4°$ (c=1%, in acetic acid).

EXAMPLE 12

L-6-ketopiperidine-2-carbonyl-L-leucyl-L-prolinamide

Step 1: L-6-Ketopipecolic acid pentafluorophenyl ester 4.3 g (30 mmoles) of L-6-ketopipecolic acid and 6.07 g (33 mmoles) of PFPOH are dissolved in 100 ml of chloroform, and 6.8 g (33 mmoles) of DCC are added to the stirred solution under ice cooling. The reaction mixture is stirred at 0° C. for one hour and then allowed to stand in a refrigerator overnight. The separated DCU is filtered off, the filtrate is evaporated, and the crystalline residue is triturated with n-hexane. The resulting 9.87 g of crude product are dissolved in 20 ml of ethyl acetate, the solution is put into a refrigerator for one hour, thereafter it is decolourized with carbon, filtered, and the filtrate is evaporated. The oily residue is dissolved in a mixture of 5 ml of ethyl acetate and 20 ml of n-hexane, the solution is allowed to stand in a refrigerator overnight, the separated crystals are filtered off. 6.34 g (68.5%) of Kpc-OPFP are obtained; m.p.: 96°–99° C., $[\alpha]_D^{25}=+30.0°$ (c=1%, in ethyl acetate).

Analysis: calculated for $C_{12}H_8O_3NF_5$ (mol.wt.: 309.20): C: 46.62%, H: 2.61%, N: 4.53%, F: 30.72%; found: C: 46.37%, H: 2.88%, N: 4.26%, F: 30.51%.

Step 2: L-6-Ketopiperidine-2-carbonyl-L-leucyl-L-prolinamide 1.32 g (5 mmoles) of H-Leu-Pro-NH$_2$.HCl are suspended in 20 ml of DMFA, and 1.61 g (5.2 mmoles) of Kpc-OPFP and 0.7 ml (5 mmoles) of triethylamine are added to the stirred suspension under ice cooling. After 5 minutes of stirring further 0.7 ml (5 mmoles) of triethylamine are added, the mixture is stirred for additional 20 minutes, and then evaporated in vacuo. The crystalline residue is triturated with ether, the crystals are filtered off, and washed with ether and cold chloroform. 1.27 g (72%) of Kpc-Leu-Pro-NH$_2$ are obtained; m.p.: 214°–216° C., $R_f^5=0.41$, $[\alpha]_D^{25}=-80.3°$ (c=1%, in acetic acid). Analysis for amino acids: $\alpha$-amino-adipic acid: 0.99 (1.0), Leu: 1.00 (1.0), Pro: 0.98 (1.0).

EXAMPLE 13

L-6-Ketopiperidine-2-carbonyl-L-norvalyl-L-prolinamide 2.38 g (9.5 mmoles) of H-Nva-Pro-NH$_2$.HCl are suspended in 30 ml of DMFA, and 3.09 g (10 mmoles) of Kpc-OPFP and 1.33 ml (9.5 mmoles) of triethylamine are added to the stirred suspension under ice cooling. After 5 minutes of stirring further 1.33 ml (9.5 mmoles) of triethylamine are added, the mixture is stirred for additional 20 minutes, and then evaporated in vacuo. The crystalline residue is triturated with ether, filtered, and washed with cold alcohol on the filter. The resulting 3.66 g of crude product are dissolved in water, the solution is decolourized, filtered, the clear filtrate is evaporated, and the crystalline residue is triturated with 10 ml of alcohol. The mixture is allowed to stand at a cool place, and then the substance is filtered off. 2.10 g (65%) of Kpc-Nva-Pro-NH$_2$ are obtained; m.p.: 192°–193° C., $R_f^5=0.31$, $[\alpha]_D^{25}=-83.2°$ (c=1%, in acetic acid).

EXAMPLE 14

D-Pyroglutamyl-L-leucyl-L-prolinamide

Step 1: Benzyloxycarbonyl-D-pyroglutamic acid pentafluorophenyl ester 4.55 g (18 mmoles) of Z-D-Glp-OH and 3.68 g (20 mmoles) of PFPOH are dissolved in 50 ml of ethyl acetate, and 4.12 g (20 mmoles) of DCC are added to the stirred solution under ice cooling. The reaction mixture is stirred at 0° C. for one hour, the separated DCU is filtered off, the filtrate is evaporated, and the oily residue is crystallized from n-hexane. The resulting 7.3 g of crude product are dissolved in 20 ml of ethyl acetate, the solution is stored in a refrigerator for one hour, decolourized with carbon, filtered, and the filtrate is evaporated. The oily residue is dissolved in 5 ml of ethyl acetate, and the product is precipitated from the solution with 20 ml of n-hexane. 6.60 g (85%) of Z-D-Glp-OPFP are obtained; m.p.: 81°–82° C., $R_f^1=0.84$, $[\alpha]_D^{25}=+40.1°$ (c=1%, in ethyl acetate).

Analysis: calculated for $C_{19}H_{12}O_5NF_5$ (mol.wt.: 429.30): C: 53.16%, H: 2.82%, N: 3.26%, F: 22.13%; found: C: 53.28%, H: 3.04%, N: 3.02%, F: 21.86%.

Step 2: Benzyloxycarbonyl-D-pyroglutamyl-L-leucyl-L-prolinamide 3.24 g (12.3 mmoles) of H-Leu-Pro-NH$_2$.HCl are suspended in 50 ml of DMFA, and 5.6 g (13 mmoles) of Z-D-Glp-OPFP and 1.72 ml (12.3 mmoles) of triethylamine are added to the stirred suspension under ice cooling. After 5 minutes of stirring further 1.72 ml (12.3 mmoles) of triethylamine are added, the mixture is stirred for additional 20 minutes, and then evaporated in vacuo. The residue is dissolved in 120 ml of chloroform, the solution is shaken twice with 30 ml of n hydrochloric acid, each, thrice with 30 ml of n sodium hydrocarbonate solution, each, and then with 30 ml of water, dried over anhydrous sodium sulfate, and finally evaporated. The oily residue is crystallized from ether to obtain 5.31 g of crude product. This crude product is boiled in 50 ml of ethyl acetate, the suspension is stored in a refrigerator for 3 hours, and the precipitate is filtered off. 4.61 g (80%) of Z-D-Glp-Leu-Pro-NH$_2$ are obtained; m.p.: 189°–194° C., $R_f^4=0.44$, $[\alpha]_D^{25}=-31.2°$ (c=1%, in acetic acid).

Step 3: D-Pyroglutamyl-L-leucyl-L-prolinamide 4.48 g (9.5 mmoles) of Z-D-Glp-Leu-Pro-NH$_2$ are dissolved in 200 ml of methanol, 0.9 g of a 10% palladium-on-carbon catalyst are added to the solution, and hydrogen is bubbled through the mixture for one hour. The catalyst is filtered off, the filtrate is evaporated, and the amorphous residue is triturated with ether. The resulting 3.07 g of crude product are dissolved in water, the solution is decolourized, filtered, and the clear filtrate is freeze-dried. 2.90 g (90.5%) of D-Glp-Leu-Pro-NH$_2$ are obtained; $R_f^5=0.40$, $[\alpha]_D^{25}=-23.6°$ (c=1%, in acetic acid).

EXAMPLE 15

Orotyl-L-histidyl-L-pipecolic acid amide

Step 1: Orotyl-L-histidine methyl ester 24.2 g (100 mmoles) of H-His-OMe.2HCl are dissolved in 120 ml of a 1:1 mixture of DMFA and dioxane, and 17.41 g (100 mmoles) of orotic acid monohydrate are added to the solution. The solution is cooled to 0° C., and 11.5 g (100 mmoles) of N-hydroxy-succinimide, 11.1 ml (100 mmoles) of N-methylmorpholine and finally 20.6 g (100 mmoles) of DCC are added. The reaction mixture is stirred at 0° C. for one hour and then at room temperature overnight. Thereafter the mixture is stored in a refrigerator for 2 hours, the separated DCU is filtered off, and the filtrate is evaporated. The only residue is crystallized from water, the crystals are filtered off, and washed on the filter with 5% aqueous citric acid solution and water. 11.6 g (38%) of Oro-His-OMe are obtained; m.p.: 258°–262° C., $R_f^5=0.40$.

Analysis: calculated for $C_{12}H_{13}O_5N_5$ (mol.wt.: 307.27): N: 22.79%; found: N: 22.51%.

Step 2: Orotyl-histidine-hydrazide 9.21 g (30 mmoles) of Oro-His-OMe are dissolved in 120 ml of DMFA, and 7.35 ml (150 mmoles) of hydrazine hydrate are poured into the solution. The reaction mixture is allowed to stand at room temperature for 2 days, then it is diluted with 100 ml of ethyl acetate and stored in a refrigerator overnight. The separated precipitate is filtered off, and the crude product is recrystallized from methanol. 8.07 g (88%) of Oro-His-N$_2$H$_3$ are obtained; m.p.: 250°–260° C., $R_f^5=0.35$.

Analysis: calculated for $C_{11}H_{13}O_4N_7$ (mol.wt.: 307.28): N: 31.91%; found: N: 30.75%.

Step 3: Orotyl-L-histidyl-L-pipecolic acid amide 5.0 g (16.28 mmoles) of Oro-His-N$_2$H$_3$ are suspended in 135 ml of DMFA, and 5.99 ml of a 8.1 n solution of hydrochloric acid in dioxane (=48.84 mmoles of HCl) are poured into the suspension. The resulting solution is cooled to −15° C., and 2.13 ml (17.9 mmoles) of tert.- butylnitrite are added dropwise with stirring. Thereafter the mixture is stirred at −10° C. for 20 minutes, and 4.56 ml (32.56 mmoles) of triethylamine, a solution of 2.05 g (16.28 mmoles) of H-Pip-NH$_2$ in 10 ml of DMFA, and finally further 2.28 ml (16.28 mmoles) of triethylamine are added dropwise to the mixture at −10° C. When the addition is complete, the mixture is stirred at −10° C. for one further hour, and then allowed to stand at 2° C. overnight. The precipitate is filtered off, the filtrate is evaporated in vacuo, and the residue is triturated with ethyl acetate. 4.6 g (74%) of crude product are obtained. 1.3 g of this product are applied onto a column filled with a 1:1 mixture of carboxymethyl cellulose 23 and carboxymethyl cellulose 52, and the column is eluted with 0.005 to 0.1 molar aqueous ammonium acetate solution (pH=5). The fractions which contain the pure product are combined and freeze-dried to obtain 820 mg of amorphous Oro-His-Pip-NH$_2$; R$_f^5$=0.10, $[\alpha]_D^{24}$=−19.0° (c=1%, in water). Analysis for amino acids: His: 1.00 (1.0), Pip: 0.94 (1.0).

EXAMPLE 16

Orotyl-L-histidyl-D-pipecolic acid amide 5.0 g (16.28 mmoles) of Oro-His-N$_2$H$_3$ are suspended in 135 ml of DMFA, and 5.99 ml of a 8.1 n solution of hydrochloric acid in dioxane (=48.84 mmoles of HCl) are poured into the suspension. The resulting solution is cooled to −15° C., and 2.13 ml (17.9 mmoles) of tert.-butylnitrite are added dropwise with stirring. Thereafter the mixture is stirred at −10° C. for 20 minutes, and 4.56 ml (32.56 mmoles) of triethylamine, a solution of 2.05 g (16.28 mmoles) of H-D-Pip-NH$_2$ in 10 ml of DMFA, and finally further 2.28 ml (16.28 mmoles) of triethylamine are added dropwise to the mixture at −10° C. When the addition is complete, the mixture is stirred at −10° C. for one further hour, and then allowed to stand at 2° C. overnight. The precipitate is filtered off, the filtrate is evaporated in vacuo, and the residue is triturated with ethyl acetate. 4.1 g (66%) of a crude product are obtained. 1.3 g of this product are applied onto a column filled with a 1:1 mixture of carboxymethyl cellulose 23 and carboxymethyl cellulose 52, and the column is eluted with 0.005 to 0.1 molar aqueous ammonium acetate solutions (pH=5). The fractions which contain the pure product are combined and freeze-dried to obtain 795 mg of amorphous Oro-His-D-Pip-NH$_2$; R$_f^5$=0.10, $[\alpha]_D^{24}$=+13.5° (c=1%, in water). Analysis for amino acids: His: 1.00 (1.0), Pip: 0.96 (1.0).

EXAMPLE 17

Orotyl-L-histidyl-L-homoprolinamide 5.0 g (16.28 mmoles) of Oro-His-N$_2$H$_3$ are suspended in 135 ml of DMFA, and 5.99 ml of a 8.1 n solution of hydrochloric acid in dioxane (=48.84 mmoles of HCl) are poured into the suspension. The resulting solution is cooled to −15° C., and 2.13 ml (17.9 mmoles) of tert.-butylnitrite are added dropwise with stirring. Thereafter the mixture is stirred at −10° C. for 20 minutes, and 4.56 ml (32.56 mmoles) of triethylamine, a solution of 2.05 g (16.28 mmoles) of H-HPro-NH$_2$ in 10 ml of DMFA, and finally further 2.28 ml (16.28 mmoles) of triethylamine are added dropwise to the mixture at −10° C. When the addition is complete, the mixture is stirred at −10° C. for one hour more, and then allowed to stand at 2° C. overnight. The precipitate is filtered off, the filtrate is evaporated in vacuo, and the residue is triturated with ethyl acetate. 4.2 g (67%) of a crude product are obtained. 1.3 g of this product are applied onto a column filled with a 1:1 mixture of carboxymethyl cellulose 23 and carboxymethyl cellulose 52, and the column is eluted with 0.005 to 0.1 molar aqueous ammonium acetate solutions (pH=5). The fractions which contain the pure product are combined and freeze-dried to obtain 802 mg of amorphous Oro-His-HPro-NH$_2$; R$_f^5$=0.10, $[\alpha]_D^{24}$=−12.8° (c=1%, in water). Analysis for amino acids: His: 1.00 (1.0), HPro: (1.0).

EXAMPLE 18

L-6-Ketopiperidine-2-carbonyl-L-norvalyl-L-thiazolidine-4-carboxylic acid amide 2.55 g (9.5 mmoles) of H-Nva-Tca-NH$_2$.HCl are suspended in 30 ml of DMFA, and 3.09 g (10 mmoles) of Kpc-OPFP and 1.33 ml (9.5 mmoles) of triethylamine are added to the stirred suspension under ice cooling. After 5 minutes of stirring further 1.33 ml (9.5 mmoles) of triethylamine are added to the reaction mixture, the mixture is stirred for additional 20 minutes, and then evaporated in vacuo. The oily residue is covered with ether and stored in a refrigerator overnight, whereupon the product crystallizes. The crystals are filtered off, washed with ether and cold alcohol, and the crude product, weighing 3.25 g, is dissolved in water. The solution is decolourized, filtered, the filtrate is evaporated, and the crude residue is triturated with 20 ml of ethanol. This mixture is allowed to stand at a cool place overnight, and the solid is filtered off. 2.0 g (59%) of Kpc-Nva-Tca-NH$_2$ are obtained; m.p.: 183°–185° C., R$_f^5$=0.47, $[\alpha]_D^{25}$=−136.0° (c=1%, in acetic acid).

EXAMPLE 19

L-6-Ketopiperidine-2-carbonyl-L-norvalyl-L-homoprolinamide

Step 1: tert.-Butoxycarbonyl-L-homoprolinamide 2.29 g (10 mmoles) of BOC-HPro-OH are dissolved in 30 ml of ethyl acetate, 1.4 ml (10 mmoles) of triethylamine are added to the solution, the mixture is cooled to −10° C., and then 1.3 ml (10 mmoles) of isobutyl chloroformate are added dropwise. After 15 minutes of stirring gaseous ammonia is introduced into the reaction mixture for 0.5 hours at −10° C., and then the mixture is allowed to stand at 0°–5° C. for 2 hours. The precipitate is filtered off, the filtrate is evaporated, and the oily residue is dissolved in 30 ml of chloroform. This solution is washed twice with 10 ml of n hydrochloric acid, each, twice with 10 ml of n sodium hydrocarbonate solution, each, and then with 10 ml of water, dried over anhydrous sodium sulfate, and evaporated. The oily residue is crystallized from n-hexane to obtain 1.95 g of a crude product. This crude product is recrystallized from a mixture of ethyl acetate and ether to obtain 1.78 g (78%) of BOC-HPro-NH$_2$; m.p.: 138°–140° C., R$_f^2$=0.43, $[\alpha]_D^{25}$=−24.85° (c=1%, in acetic acid).

Analysis: calculated for C$_{11}$H$_{20}$O$_3$N$_2$ (mol.wt.: 228.29): C: 57.87%, H: 8,83%, N: 12.27%; found: C: 57.60%, H: 8,89%, N: 12.11%.

Step 2: L-Homoprolinamide hydrochloride 1.6 g (7 mmoles) of BOC-HPro-NH$_2$ are dissolved in 10 ml of warm ethyl acetate. The solution is cooled to room temperature, and 10 ml of a 6 n hydrochloric acid solution in ethyl acetate are added. The reaction mixture is allowed to stand for one hour, thereafter it is diluted with ether, the separated precipitate is triturated and filtered off. 1.05 g (91%) of H-HPro-NH$_2$.HCl are obtained; m.p.: 178°–180° C., $R_f^6$=0.32, $[\alpha]_D^{25}$=+26.2° (c=1%, in methanol).

Step 3: L-Norvalyl-L-homoprolinamide hydrochloride 0.99 g (6 mmoles) of H-HPro-NH$_2$.HCl is suspended in 20 ml of DMFA, and 0.84 ml (6 mmoles) of triethylamine and 2.3 g (6 mmoles) of BOC-Nva-OPFP are added to the suspension with stirring. After 15 minutes further 0.84 ml (6 mmoles) of triethylamine are introduced, the mixture is stirred for additional one hour, and then it is evaporated in vacuo. The residue is dissolved in 50 ml of chloroform, the solution is washed twice with 10 ml of n hydrochloric acid, each, and twice with 10 ml of n sodium hydrocarbonate solution, each, dried over anhydrous sodium sulfate and then evaporated. The oily residue is dissolved in 6 ml of ethyl acetate, and 10 ml of a 6 n hydrochloric acid solution in ethyl acetate are added. After one hour of standing the mixture is diluted with ether, the separated amorphous precipitate is triturated with the solvent, filtered off, and dried in vacuo over anhydrous sodium hydroxide, 1.22 g (89.5%) of H-Nva-HPro-NH$_2$.HCl are obtained; $R_f^5$=0.12.

Step 4: L-6-Ketopiperidine-2-carbonyl-L-norvalyl-L-homoprolinamide 1.22 g (5.37 mmoles) of H-Nva-HPro-NH$_2$.HCl are dissolved in 20 ml of DMFA, and 0.75 ml (5.37 mmoles) of triethylamine and 1.7 g (5.5 mmoles) of Kpc-OPFP are added to the solution. After 5 minutes of stirring further 0.75 ml (5.37 mmoles) of triethylamine are introduced, the mixture is stirred for additional 20 minutes, and then evaporated in vacuo. The residue is triturated with ether, the separated 1.8 g of amorphous crude product are applied onto a column filled with 40 g of silica gel, and the column is eluted with solvent mixture (4). 1.11 g of the desired product are isolated from the fractions which contain this compound in pure state. This substance is dissolved in water, the solution is decolourized, filtered, and the clear filtrate is freeze-dried. 1.0 g (53%) of Kpc-Nva-HPro-NH$_2$ is obtained; $R_f^5$=0.35, $[\alpha]_D^{25}$=−44.6° (c=1%, in acetic acid).

What we claimed is:

1. A peptide of the general formula (I)

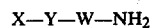 X—Y—W—NH$_2$       (I)

wherein

X is a L-pyroglutamyl, D-pyroglutamyl, L-2-ketoimidazolidine-4-carbonyl, L-6-keto-pipecolyl, L-thiazolidine-4-carbonyl, L-prolyl or orotyl group, Y is L-leucyl or L-norvalyl and W is a D-prolyl, L-thiazolidine-4-carbonyl, L-homoprolyl, L-leucyl, L-isoleucyl, L-methionyl, L-pipecolyl or D-pipecolyl group, or the W-NH$_2$ group stands for a pyrrolidyl or piperidyl group, or a pharmaceutically acceptable complex thereof.

2. L-Pyroglutamyl-L-leucyl-L-pipecolic acid amide.

3. L-Pyroglutamyl-L-leucyl-L-thiazolidin-4-carboxylic acid amide.

4. L-Pyroglutamyl-L-norvalyl-L-thiazolidin-4-carboxylic acid amide.

5. L-2-Ketoimidazolidine-4-carbonyl-L-leucyl-L-prolinamide.

6. L-6-Ketopiperidine-2-carbonyl-L-leucyl-L-prolinamide.

7. L-6-Ketopiperidine-2-carbonyl-L-norvalyl-L-prolinamide.

8. D-Pyroglutamyl-L-leucyl-L-prolinamide.

9. L-6-Ketopiperidine-2-carbonyl-L-norvalyl-L-thiazolidine-4-carboxylic acid amide.

10. L-6-Ketopiperidine-2-carbonyl-L-norvalyl-L-homoprolinamide.

11. A pharmaceutical composition for use in (a) decreasing the duration of sleeping caused by barbituates or alcohol and/or (b) suppressing hypothermy provoked by various drugs and/or (c) increasing locomotive activity and/or (d) inhibiting catalepsy provoked by Haloperidol comprising an effective amount of an active ingredient comprising at least one compound of the formula X—Y—W—NH$_2$ wherein X is a L-pyroglutamyl, D-pyroglutamyl, L-2-ketoimidazolidine-4-carbonyl, L-6-keto-pipecolyl, L-thiazolidine-4-carbonyl, L-propyl or orotyl group, Y is L-leucyl or L-norvalyl, and W is a D-propyl, L-thiazolidine-4-carbonyl, L-homoprolyl, L-leucyl, L-isoleucyl, L-methionyl, L-pipecolyl or D-pipecolyl group, or the W—NH$_2$ group stands for a pyrrolidyl or piperidyl group or a pharmaceutically acceptable complex thereof and a pharmaceutical carrier or diluent.

* * * * *

UNITED STATES PATENT AND TRADEMARK OFFICE
CERTIFICATE OF CORRECTION

PATENT NO. : 4,386,073

DATED : May 31, 1983

INVENTOR(S) : Lajos Kisfaludy; Tamas Szirtes, Lajos Balaspiri; Eva Palosi; Laszlo Szporny; and Adam Sarkadi It is certified that error appears in the above-identified patent and that said Letters Patent is hereby corrected as shown below:

On the title page, correct line [73] to read as follows:

Assignee: Richter Gedeon Vegyeszeti Gyar Rt., Budapest, Hungary

Signed and Sealed this

Tenth Day of April 1984

[SEAL]

Attest:

GERALD J. MOSSINGHOFF

Attesting Officer

Commissioner of Patents and Trademarks